(12) United States Patent
Ryser et al.

(10) Patent No.: US 7,726,955 B2
(45) Date of Patent: Jun. 1, 2010

(54) PUMP SYSTEM

(75) Inventors: Peter Ryser, Morges (CH); Sigfrid Straessler, St-Saphorin-sur-Morges (CH); Josef Hilber, Allenwinden (CH)

(73) Assignee: Sensile Pat AG, Haegendorf (CH)

( * ) Notice: Subject to any disclaimer, the term of this patent is extended or adjusted under 35 U.S.C. 154(b) by 1070 days.

(21) Appl. No.: 10/576,780

(22) PCT Filed: Oct. 15, 2004

(86) PCT No.: PCT/IB2004/003385
§ 371 (c)(1),
(2), (4) Date: Apr. 21, 2006

(87) PCT Pub. No.: WO2005/039674
PCT Pub. Date: May 6, 2005

(65) Prior Publication Data
US 2007/0071596 A1   Mar. 29, 2007

(30) Foreign Application Priority Data
Oct. 27, 2003   (EP) .................................. 03024653

(51) Int. Cl.
*F04B 17/00* (2006.01)
(52) U.S. Cl. .................. 417/420; 417/423.1; 415/172.1; 415/170.1; 604/891.1
(58) Field of Classification Search ................. 417/420, 417/423.1, 410.3, 410.1; 415/172.1, 170.1; 604/891.1
See application file for complete search history.

(56) References Cited

U.S. PATENT DOCUMENTS

| 3,045,134 | A | * | 7/1962 | Mould, Jr. .................. 310/106 |
| 3,647,314 | A | * | 3/1972 | Laessig ..................... 415/206 |
| 4,152,098 | A | | 5/1979 | Moody et al. |
| 4,883,467 | A | | 11/1989 | Franetzki et al. |
| 5,219,276 | A | * | 6/1993 | Metzner et al. ............. 417/356 |
| 5,704,767 | A | * | 1/1998 | Johnson ...................... 417/43 |
| 6,179,596 | B1 | * | 1/2001 | Weisener et al. ............ 418/171 |
| 2009/0123309 | A1 | | 5/2009 | Hilber et al. |

* cited by examiner

*Primary Examiner*—Charles G Freay
*Assistant Examiner*—Peter J Bertheaud
(74) *Attorney, Agent, or Firm*—Saliwanchik, LLoyd & Saliwanchik

(57) ABSTRACT

A pump system having a pump module (10) comprising a stator housing (28) with a chamber (30), a rotor (32) rotatably and axially slidably received in the chamber and comprising a first axial extension (46) with a liquid supply channel (50) and a second axial extension with a liquid supply channel (52), the first and second axial extensions having different diameters, and first and second sealing rings (54, 56), mounted around the first and second axial extensions.

17 Claims, 6 Drawing Sheets

PUMP SYSTEM

FIELD OF THE INVENTION

The present invention relates to a pump system for subcutaneous delivery of a liquid pharmaceutical product for humans. The pharmaceutical product to be delivered may in particular be insulin for diabetic patients.

BACKGROUND OF INVENTION

One approach to intensive insulin therapy is a continuous subcutaneous insulin infusion utilizing an external insulin infusion pump. The portable pump is connected to the patient via a flexible tube attached at one end to the pump and at the other end to a patch with a needle for subcutaneous injection. The patch typically comprises an adhesive to adhere to the patient's skin. The patch with needle is typically provided with a short section of transparent flexible tube through which the insulin is supplied to the patient, the tube extending from the needle to a connector for connection to a complementary connector at the end of a flexible tube extending from the insulin pump. This enables the patch with needle to be regularly changed, for example every three days. The insulin is supplied in a disposable cartridge with a reserve of insulin that may last for three days to three weeks depending on the patient's insulin requirement. The patch with needle is thus changed more often than the insulin cartridge. At each change of patch with needle or of the insulin cartridge, the flexible supply tube or section of tube must be filled with insulin and any air removed prior to subcutaneous injection. Many precautions must be taken when changing the insulin cartridge, and a rigorous procedure must be followed. There is therefore a risk of false manipulation in existing insulin pump systems, particularly when components are replaced. Risks of errors are increased by the need to change the patch at intervals different to those required for the insulin cartridge.

A further disadvantage of the existing insulin pumps is that, in spite of their portability, they are not sufficiently compact and light to be carried without a certain discomfort and inconvenience. Moreover, the size of the existing insulin pumps does not allow them to be easily positioned close to the point of injection. They thus require fairly long flexible supply tubes, with the disadvantages this confers, when considering the need to evacuate the air from the tubes, and the high cost of the tubes when replacement is needed.

Another important disadvantage of existing insulin pumps is that they are unable to pump very small quantities of liquid with sufficient precision to allow the insulin in the cartridge to have a higher concentration thus enabling a longer interval between cartridge changes and/or reduction in the size of the cartridge. The limited precision of conventional pumps is thus a limiting factor on the miniaturization of the pump and the length of intervals between cartridge changes. The aforementioned factors also adversely affect the portability of the device and the high risk of manipulation error by patients in view of the long supply tubes and the need to change different interconnected elements, such as the cartridge, the flexible tube and the patch with needle. Each connection and disconnection operation requires a procedure to be followed and precautions to be taken by the patient, which are subject to a certain risk of false manipulation.

BRIEF SUMMARY OF THE INVENTION

Considering the aforegoing, an object of the present invention is to provide a pump system for the subcutaneous delivery of liquid medicaments, such as insulin, that is reliable, compact and safe.

It is an advantage to provide a pump that is easy to use and where the risk of false manipulations by a patient or medical practitioner is reduced.

It is an advantage to provide an insulin pump that is comfortable to carry and increases the range of activities that the patient can engage in.

It is advantageous to provide an insulin pump at low cost.

Objects of this invention have been achieved by providing a pump system for the subcutaneous delivery of liquid medicaments according to claim 1.

Disclosed herein is a pump system for subcutaneous delivery of a liquid medicament, comprising a reservoir, a pump module, and an electronic control and communication module.

The pump module comprises a rotor received in a cavity of a stator housing element, plugged on or integrally formed with the reservoir. Torque to rotate the rotor is provided by magnetic induction coils mounted in a stator section acting on permanent magnets mounted in the rotor, and connected to a microprocessor of the electronic control and communication means.

Sealing rings are mounted around first and second axial extensions of the rotor and are lodged in complementary bearing surfaces of the stator housing. The sealing rings, which may advantageously consist of simple O-ring seals, are mounted at an oblique angle with respect to a plane perpendicular to the axis of rotation of the rotor. Each axial extension of the rotor comprises a liquid supply channel, in the form of a groove. When the rotor turns, the extremity of each groove passes from one side of the sealing ring to the other side, thereby opening and closing liquid communication across the sealing ring. The liquid supply groove of each axial extension in conjunction with the corresponding sealing ring thus forms a valve that opens and closes as a function of the angular and axial displacement of the rotor. It may be noted that the sealing rings may also act as bearings supporting the rotor element.

Over a 360° rotation cycle of the rotor, the rotor also effects an axial displacement to when one and the other sealing ring valve respectively is open. The axial displacement of the rotor, when either valve is open, generates a pumping action due to a change in the volume occupied by the rotor in the stator housing cavity. The volume change is a result of the difference in diameter between the two axial extensions held by the sealing rings.

The axial displacement of the rotor is advantageously driven by a magnetic force generated by the motor coils which produce both an axial and a radial force component. An important feature of the pump system according to this invention is the ability to pump a very small quantity of liquid with each rotation cycle. As the liquid pumped per cycle is very small, the amount of liquid required by the patient may be pumped by rotating the rotor a large number of revolutions, which can be easily performed and controlled. A very high precision of the pump may advantageously be obtained by individual factory calibration of the pump, whereby the number of turns of the rotor that are required to pump a certain amount of liquid is measured during the calibration process and stored in a RFID transponder mounted in the pump module.

The pump rotor and stator parts may advantageously be made primarily of injected plastic material compatible with medical devices. The stator housing may be plugged on the reservoir or integrally fixed therewith to form a disposable liquid supply unit that is thrown away and replaced once the liquid medicament in the container is consumed. The motor coils and electronic control and communication unit may be mounted in a base unit to which the liquid supply unit is removably fixed.

In view of the particularly simple pump motor design, the few components and the possibility of forming the rotor and stator parts primarily out of injected medical plastics, a particularly low cost disposable pump and reservoir is formed.

An advantage of the pump according to this invention is that the major part of the pump can be mounted to the reservoir in a permanent manner, thus obviating the need for users to establish a connection between the liquid medicament reservoir and the pump. The latter eliminates the risk of false manipulations at this interface.

An important advantage of the pump system according to this invention is that that very small amounts of liquid that may be pumped per revolution of the rotor enables small doses of liquid to be injected very precisely. This allows the use of higher drug concentrations than in conventional systems, and as a consequence smaller reservoir cartridges or longer intervals between replacement of reservoir cartridges. As the pump system according to this invention is very compact, it may be positioned close to the point of subcutaneous injection, and thereby allowing the pump to be connected directly to the connector of the flexible supply tube of the injection patch.

The electronic control and communication means may advantageously comprise a transceiver for wireless communication with a control and display unit, allowing the patient to check and control operation of the pump. The electronic control and communication means advantageously further comprises a RFID reader that is mounted in the base unit and communicates with the RFID transponder mounted in the pump module in order to read the factory calibration information stored in the transponder. The RFID reader is connected to a microprocessor of the electronic control and communication module in order to provide the calibration information for accurate control of the pump. The calibration information in particular comprises the number of revolutions needed for pumping a certain volume that is specific to the pump. This information may advantageously be entered into the RFID transponder during the manufacturing process of the disposable liquid supply units comprising the reservoir and pump module, and thus ensure a particularly high precision pump.

The ability to calibrate the pump very precisely in a production assembly line according to this invention, obviates the requirement for ensuring an extremely high precision in the volume of liquid pumped per pump cycle, which in turn would require extremely high precision in manufacturing and assembly tolerances of the pump components.

Further objects and advantageous aspects of the invention will be apparent from the claims and the following detailed description of embodiments of the invention, in conjunction with the drawings in which:

DETAILED DESCRIPTION OF THE INVENTION

Figure 1A:
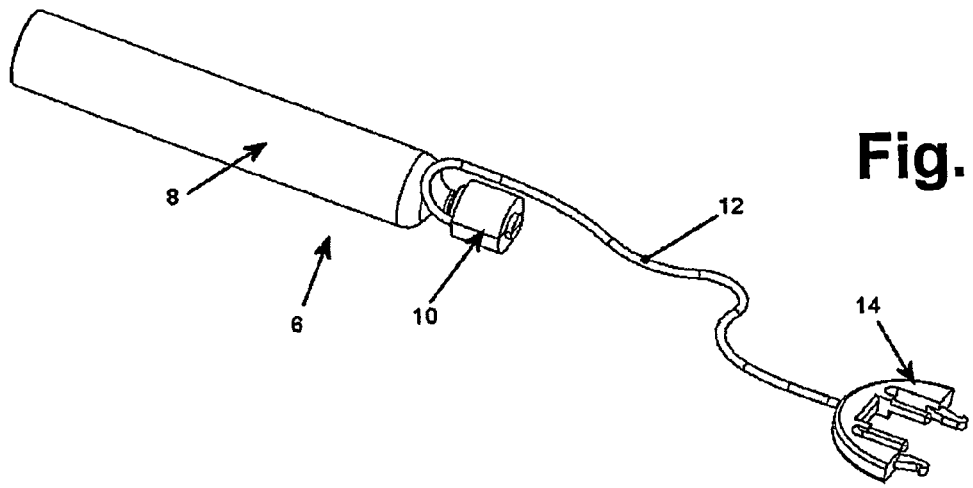
FIG. 1a is a view in perspective of a pump system according to this invention.
Figure 1B:
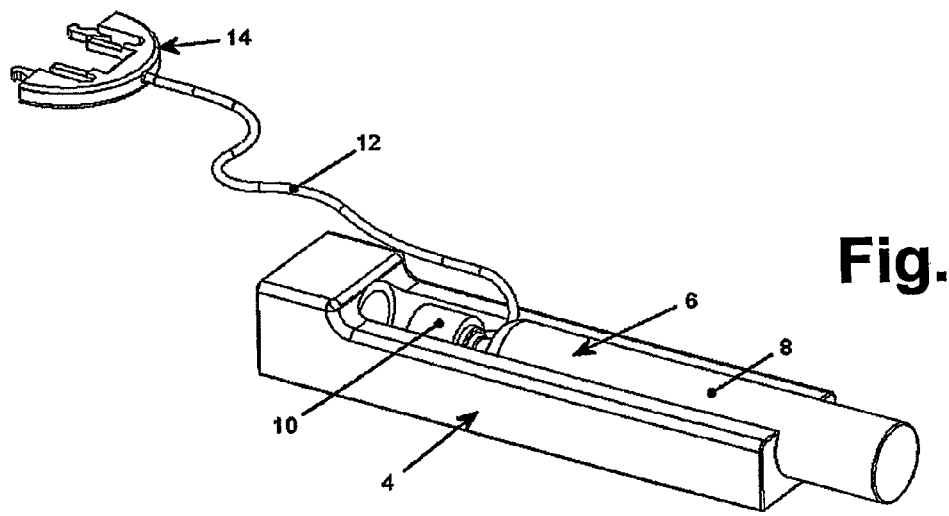
FIG. 1b is a view in perspective of a liquid supply unit of the pump system of FIG. 1a, without a base unit.
Figure 1C:
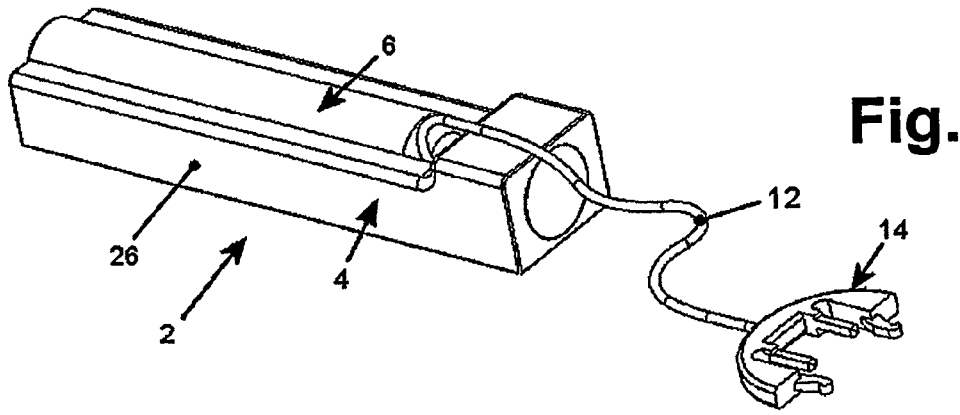
FIG. 1c is a view in perspective of a pump system according to this invention, showing the assembly of the liquid supply unit in the base unit.
Figure 2:
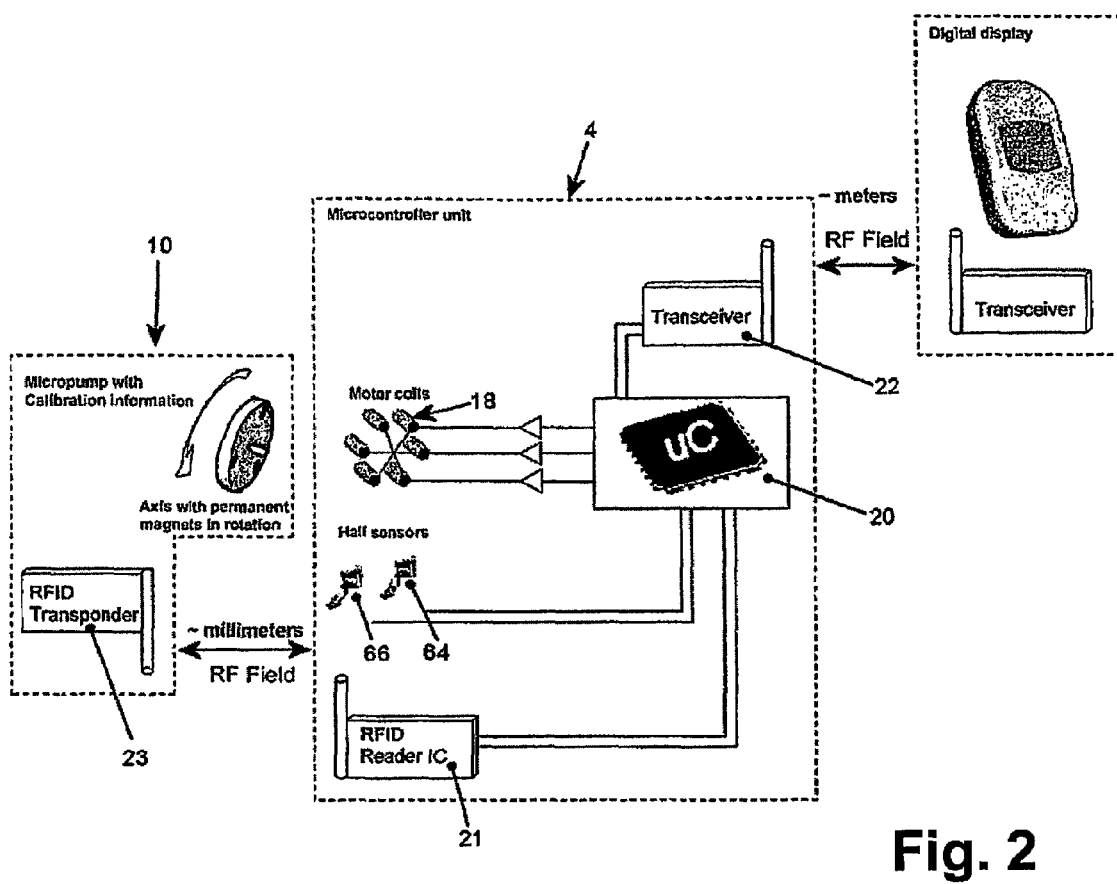
FIG. 2 is a block diagram illustrating the functional features of the pump system according to the invention.

Referring to FIGS. 1 to 3, a liquid drug delivery pump system 2 comprises a base unit 4 and a disposable liquid supply unit 6 comprising a reservoir 8, a pump module 10, a supply tube 12, and a connector 14. The connector 14 is adapted to plug to a complementary connector of a patch with injection needle for subcutaneous delivery of the liquid medicament. The liquid is pumped from the reservoir 8 into the supply tube 12 by means of the pump module 10 positioned therebetween.

The base unit 4 comprises a pump motor section 16 with magnetic induction coils 18 connected to an electronic control and communication module 20. The electronic control and communication module comprises a microprocessor for controlling the pump motor operation and communicating via a radio frequency (RF) transceiver 22 thereof positioned in the base unit 4, with an external control and display unit 24 that enables the remote control and verification of the pump operation. The information transmitted by the control and communication module 20 of the base unit 4 would for example include a log of the pump operation (time of operation and volume pumped) and any alarm signals arising from faulty operation. The RF transceiver may use existing technology for keyed digital transmission in order to ensure the absence of interference with other RF devices. Such technology is widely available and need not be further described herein.

The electronic control and communication module 20 further comprises a radio frequency identification (RFID) reader 21 connected to the microprocessor 20 and in wireless communication with a RFID transponder 23 mounted in the pump module. RFID transponders are known passive devices used in a number of different applications and comprise a small chip and a coil to generate electrical energy for powering the transponder from the RF field. Such transponders are for example already used on goods as identification tags.

In the present invention, the RFID transponder is mounted in the pump module, or alternatively on the reservoir or other part of the disposable liquid supply unit 6, and comprises electronic data stored in a memory of the transponder chip providing calibration information on the specific pump module. This calibration information may be entered into the transponder during production of the liquid supply unit, indicating the number of rotor revolutions required to pump a certain volume of liquid for the specific liquid supply unit.

The RFID reader 21, which is mounted in the reusable base unit 4, thus reads the calibration information stored in the RFID transponder of the pump module and provides this information to the microprocessor 20 which controls the pump motor. Great accuracy in the amount of liquid to be pumped can thus be achieved, in a reliable and economic manner.

The base unit 4 further has a support and fixing means 26 for mounting and positioning the liquid supply unit 6 thereto.

The pump module 10 of the liquid supply system 6 comprises a stator housing 28 and a rotatable rotor 30 mounted in a cavity or chamber 32, hereinafter called rotor chamber. The stator housing 28 further comprises a portion 34 for mounting the pump module to an open end 36 of the reservoir 8. A hermetic cover 38 may be positioned between the stator housing 28 and the open end 36 of the reservoir to provide a seal therebetween and prevent liquid in the reservoir from escaping. The rotor chamber 32 is in communication with the inside of the reservoir via an inlet channel in the form of a needle 42 inserted through the hermetic cover 38.

Figure 6:
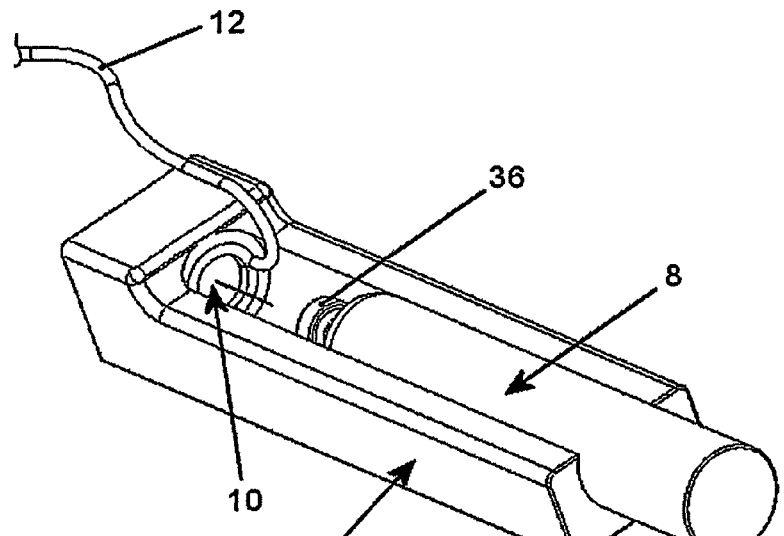
FIG. 6 is a view in perspective of another embodiment of a pump system according to this invention.

Referring to FIG. 6, in an alternate embodiment, the pump module 10 is mounted in the base unit 4 and the disposable reservoir 8 is assembled to the base unit, whereby the inlet needle 42 of the pump module is inserted through a hermetic cover 36 of the reservoir.

Referring to FIGS. 1 and 3, the rotor chamber 32 is interconnected via an outlet channel 44 to the flexible supply tube 12. The rotor 30 comprises first and second axial extensions 46, 48 having a generally cylindrical shape with diameters D1 and D2, respectively, the diameter D2 of the second axial extension 48 being superior to the diameter D1 of the first axial extension 46. The axial extensions 46, 48 are provided with channels in the form of grooves 50, 52 that allow the inlet and outlet channels 40, 44, respectively, to be in communication with the rotor chamber 32 depending on the angular and axial position of the rotor 30.

The rotor 30 is held to the stator 28 via first and second sealing rings 54, 56 that act on the one hand as valves, and on the other hand as bearings for the rotor. The first and second sealing rings are both inclined with respect to a plane perpendicular to the axis of rotation of the rotor. The angle of inclination $\phi_1, \phi_2$ of the sealing rings may be the same or may differ from each other and will preferably lie in the range of 5 to 45 degrees with respect to the plane perpendicular to the axis of rotation A. The main purpose of the inclined sealing rings is to allow liquid to flow across the seal, or to stop the flow of liquid across the seal as a function of the angular and axial position a of the rotor. This can be better understood by referring to FIG. 4, which illustrates the opening and closing function of the sealing rings as a function of the angular position of the axial extension. It may be seen that over a certain angle $\alpha_1$, the liquid supply channel 50, 52 extends across the lower part of the inclined sealing ring 54, 56, as viewed in FIG. 4. Over the angle $\alpha_1$, the seal thus leaks, in other words, forms an open valve. Rotation of the rotor will eventually cause the liquid supply channel extremity 58 to cross from the outer side of the sealing ring 60a to the inner side 60b, thus stopping the flow of liquid across the seal, in other words, closing the valve.

The angular movement is superposed by an axial movement of the rotor, which determines the axial position a of the channel extremity 58. The axial displacement of the rotor is generated by an axial magnetic force component generated by the motor coils 18 (in this embodiment, positioned in the base unit 4, and acting upon permanent magnets 62 on the rotor). The coils 18 and permanent magnet 62 also serve to generate a radial force component to generate the torque required for rotation of the rotor. Axial displacement of the rotor will occur when one of the sealing rings leaks (i.e. the sealing valve is open), whereby the polarity of the magnetic axial force component generated by the motor coils 18 on the rotor is such that when the first sealing ring valve 50,54 is open (leaks), the rotor is axially biased, towards the second sealing ring 56 (to the right as shown in FIG. 3b). It may be noted that when the first sealing ring valve 50,54 leaks, the other sealing ring valve 52,56 is closed, and vice versa.

In this particular embodiment, the axial displacement of the rotor to the right causes the volume in the rotor chamber 32 to increase, thereby drawing in liquid from the reservoir, through the inlet 40 (since the first sealing ring valve 50,54 is open). Further rotation of the rotor closes the first sealing ring valve 50,54, whereby over an angle β both sealing ring valves 50,54,52,56 are closed. The purpose of having both sealing ring valves closed over a certain transition angle β, is to ensure that both sealing ring valves are never open simultaneously, particularly when taking into account certain manufacturing tolerances of the rotor, stator, and sealing rings. It would be unacceptable to have both sealing rings open at the same time, since this would allow the direct and uncontrolled flow of liquid from the reservoir to the patient.

In view of the incompressibility of the fluid in the rotor chamber, whilst both sealing valves are closed the axial displacement of the rotor is not possible. In this regard, it is advantageous to apply a magnetic force on the rotor with the motor coils, since the magnitude of the force is well controlled and essentially not dependent on the axial position of the rotor.

Over a 360° rotation cycle of the rotor 30, the first sealing ring valve 50,54 will open over an angle $\alpha_1$ less than 180°, during which time the rotor will axially displace towards the other sealing ring, thus drawing in fluid into the rotor chamber 32 and simultaneously pumping a certain volume $V_2$ through the outlet 44.

Figure 3A:
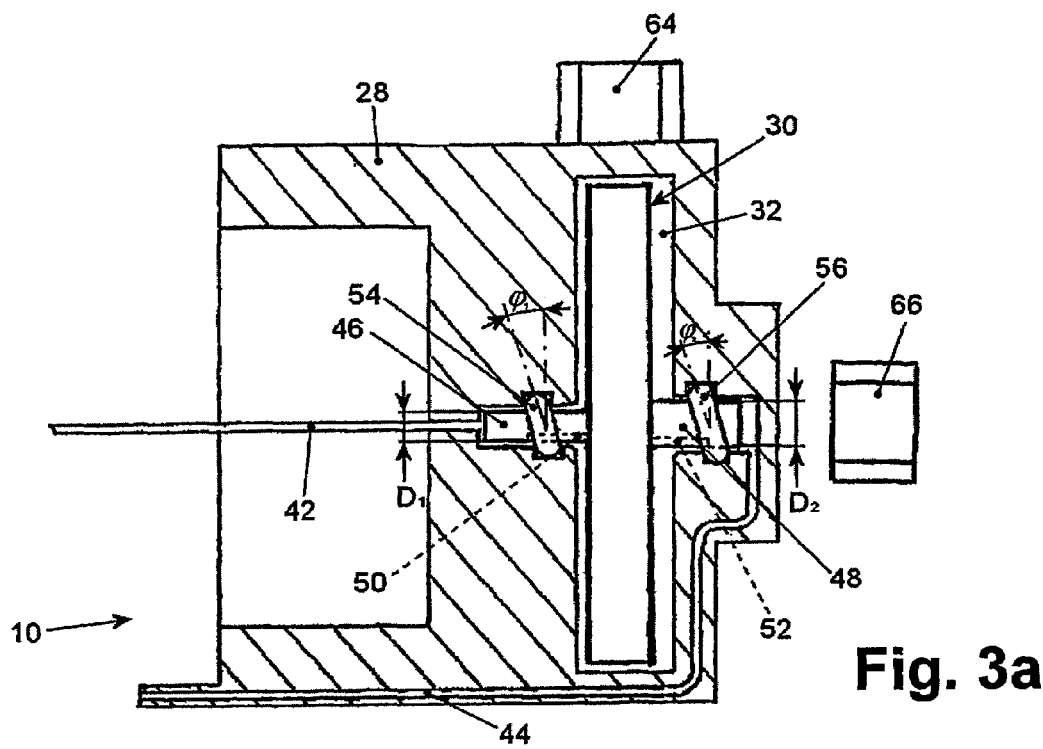
FIG. 3a is a view in cross-section of part of the pump module of the pump system according to this invention, with the rotor in a rearward axial position.
Figure 3B:
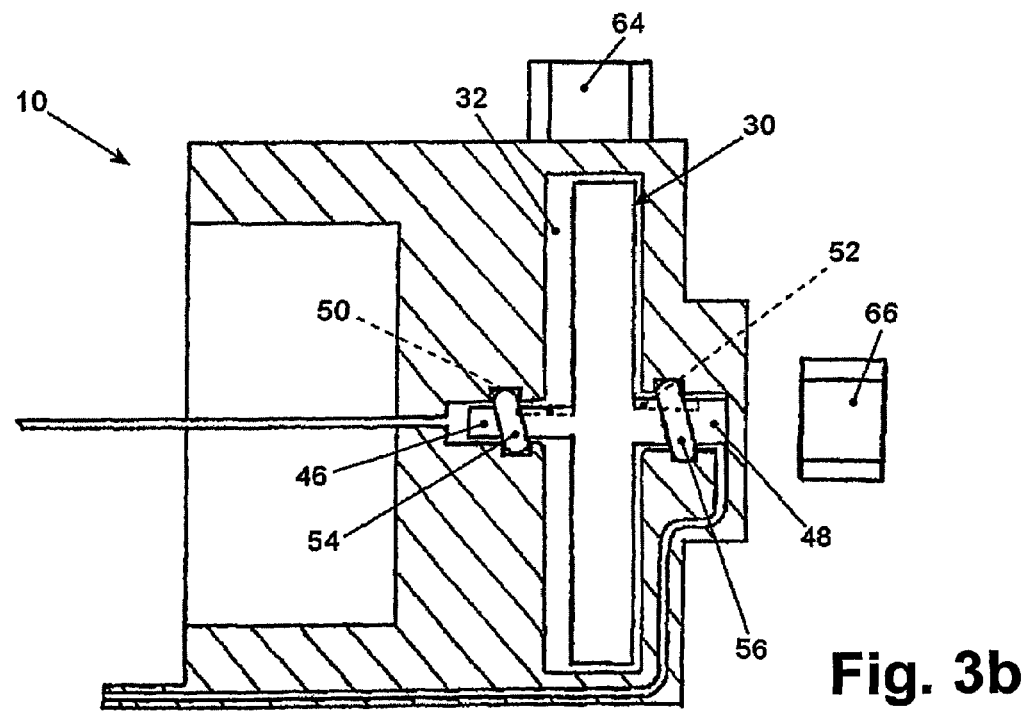
FIG. 3b is a view similar to FIG. 3a with the rotor in the forward axial position.
Figure 3C:
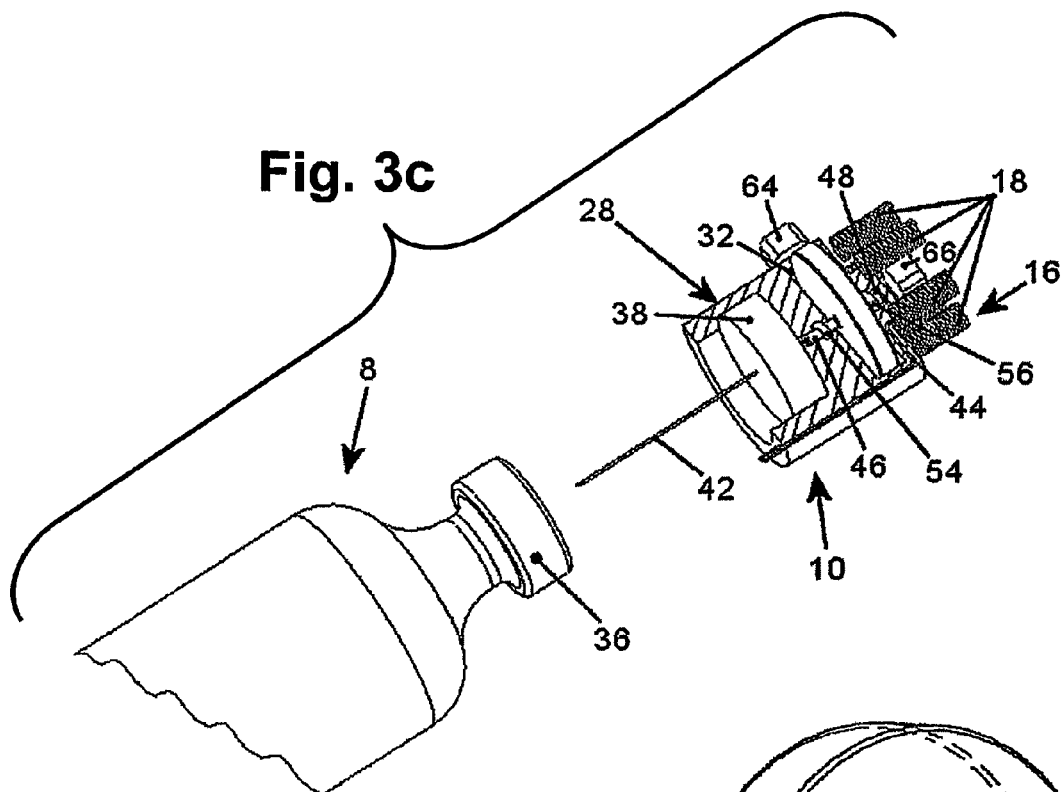
FIG. 3c is a cross section of view in perspective of the pump module of FIGS. 3a and 3b about to be mounted on a reservoir.
Figure 3D:
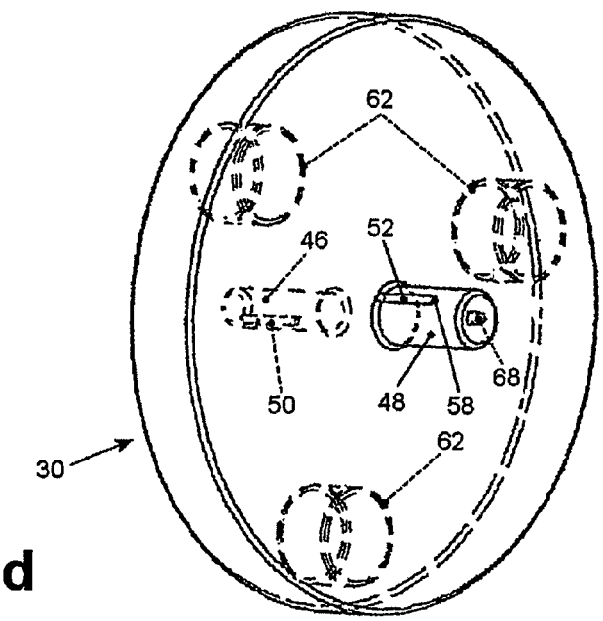
FIG. 3d is a view in perspective of the rotor of the pump module, hidden details being shown in dotted lines.
Figure 5:
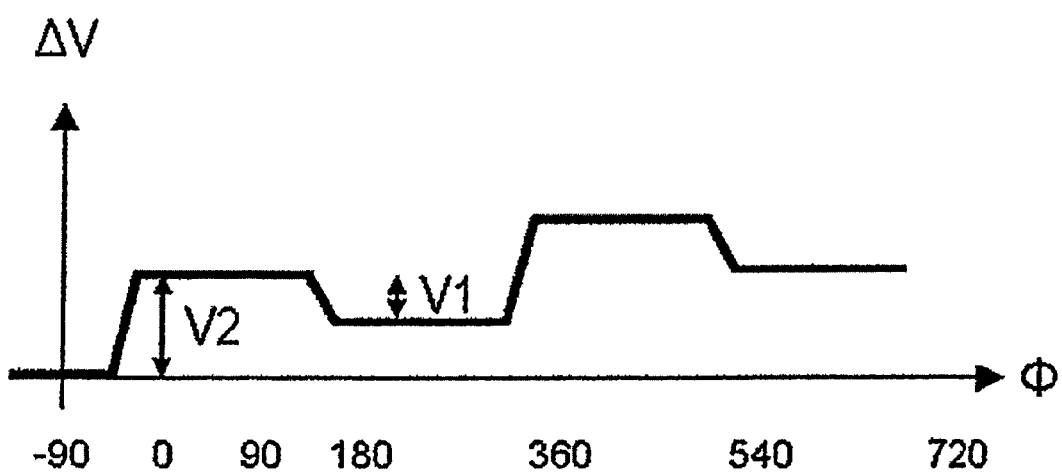
FIG. 5 is a graph illustrating the volume of liquid pumped as a function of the angular displacement of the rotor of the pump.

The second sealing ring valve 52,56 opens over an angle $\alpha_2$ less than 180°, when the first sealing ring valve 50,54 is closed, whilst the magnetic axial force component drives the rotor towards the first sealing ring until the position shown in FIG. 3a. The axial movement of the rotor, which causes the volume in the chamber 32 to reduce, draws a volume $V_1$ of fluid from the outlet channel 44 back into the cavity portion 64 of the outlet channel lodging the second axial extension 48. As the volume $V_1$ drawn back is smaller than the volume $V_2$ that was pumped out of the outlet, each 360° cycle of the rotor causes a volume $$\Delta V = V_2 - V_1$$

to flow to the patient, as best illustrated in FIG. 5.

Figure 4:
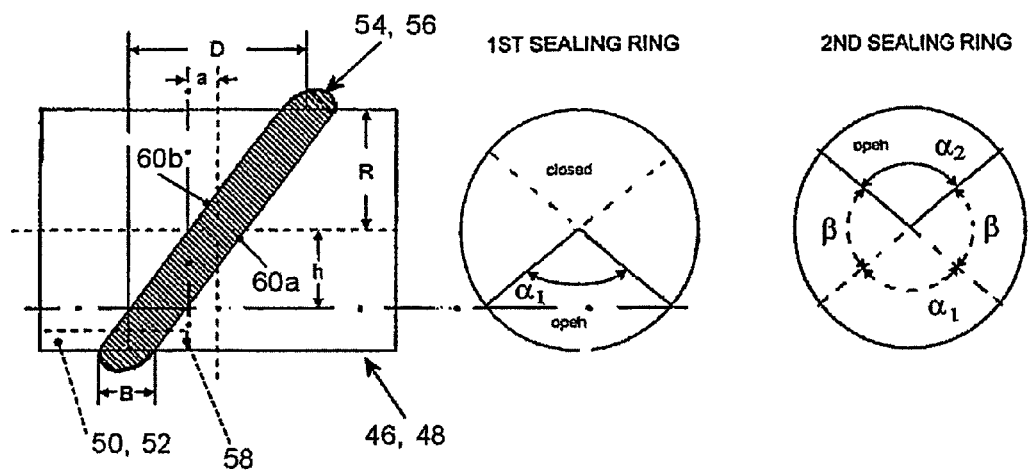
FIG. 4 is an illustration of an axial extension of the rotor, showing the open and closed position of the liquid supply channel across the sealing ring.

The angle F (stated in radians) over which one of the sealing ring valves is closed, as a function of the axial position a of the channel, the width B of the sealing, the axial width D of the center line of the sealing ring as shown in FIG. 4, may be expressed as follows:

$$F=2\pi(\tfrac{1}{2}+1/\pi \operatorname{ArcSin}[(2a+B)/D])$$

As an example, the values of the above-mentioned dimensions for an insulin pump made according to this invention could be in the order of:
Overall outside diameter of the pump module stator≈9 mm
Rotor diameter≈6 mm
Width of the rotor≈2 mm
$\Delta V = 10-50 \cdot 10^{-9}$ l (nanolitres)
Typical values for the parameters B, D and a could for example be as follows:
B≈5–20 µ
D≈0.2–0.5 mm
a≈0.1–0.2 mm
Diameter D1 of first axial extension≈0.6 mm
Diameter D2 of second axial extension≈0.4 mm
In this case, $\Delta V \approx 10 \cdot 10^{-9}$ l (nanolitres).

In order to verify the correct functioning of the pump, position sensors 64, 66 may be mounted to the stator housing 28 and motor section 16 of the base unit 4 to determine, respectively, the number of rotation cycles of the rotor and the axial position of the rotor. These position sensors may for example be Hall-effect sensors that would detect the presence of the magnetic field of a permanent magnet embedded in the rotor. For example, a permanent magnet 68 embedded in the axial extension 48 (see FIG. 3d) would allow the Hall sensor 66 to determine when the rotor of 32 is in the extreme right position, as shown in FIG. 3b. The angular position sensor 64 can be used to detect the passage of the permanent magnets 62 mounted in the rotor and thus act as a counter to determine the number of cycles of rotation of the rotor.

The rotor 30 may advantageously comprise three or more permanent magnets 62 spaced equally around the periphery of the rotor and embedded therein, for example by plastic injection overmoulding of the rotor body around the magnets. The pump motor section 16 in the base unit may advantageously comprise a plurality of coils, for example six coils 18, arranged and controlled so as to function, in conjunction with the rotor permanent magnets, as a stepping motor which can be easily controlled by the electronic control and communications module.

Figure 7:
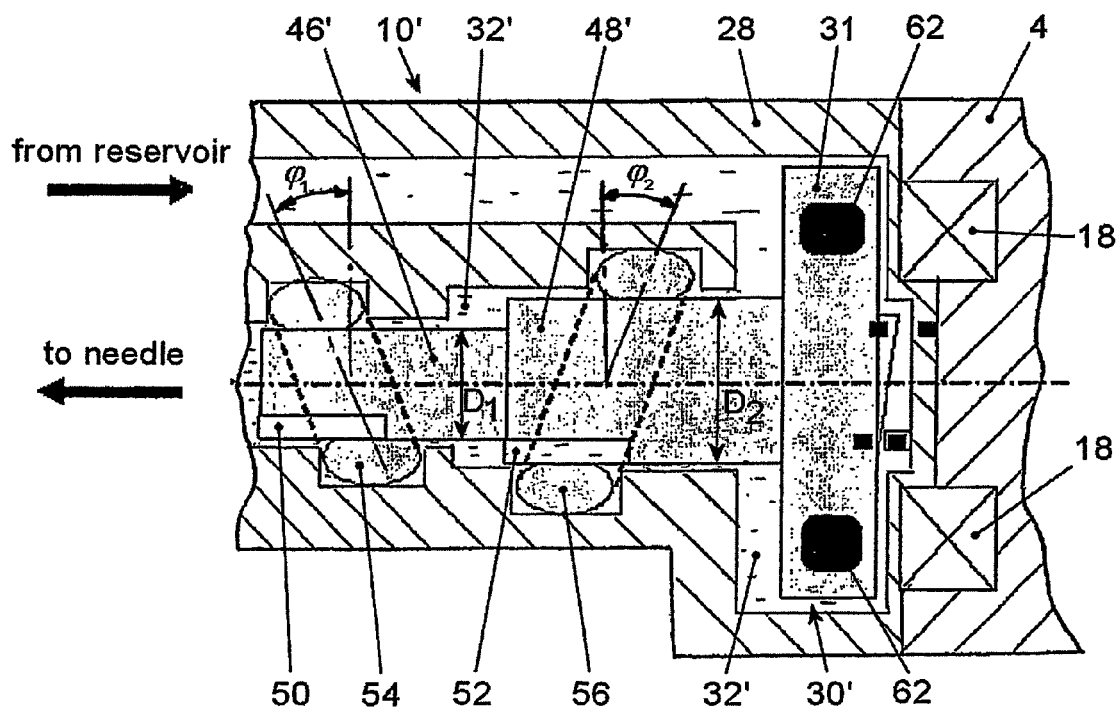
FIG. 7 is a partial cross-sectional view of another variant of a pump module of a pump system according to this invention.

Referring to FIG. 7, a variant of the pump module 10' is shown. The main difference with the previously described embodiment is that the first and second axial extensions 46', 48' are adjacent and extend from the same side of the rotor body 31. The rotor 30' is rotatably and axially slidably supported by the sealing rings 54, 56 and generates a pumping action by the change in the volume of the chamber 32' located between the sealing rings in conjunction with the opening and closing of the channels 50, 52 in essentially the same manner as the previously described embodiment. Elements of this variant that are similar to those of the first embodiment are referenced with the same numerals.

The invention claimed is:

1. A pump system for the pumping of a liquid, having a pump module comprising:
    a stator housing with a chamber,
    a rotor rotatably and axially slidably received in the chamber and comprising a first axial extension comprising a liquid supply channel and a second axial extension comprising a liquid supply channel, the first and second axial extensions having different diameters, and
    first and second sealing rings, mounted around the first and second axial extensions,
    said liquid supply channel of each axial extension in conjunction with the corresponding sealing ring forming a valve that opens an closes as a function of the angular and axial displacement of the rotor.

2. The pump system according to claim 1, wherein the first and second sealing rings are mounted at an oblique angle with respect to a plane perpendicular to an axis of rotation of the rotor.

3. The pump system according to claim 1, wherein the sealing rings are O-ring seals.

4. The pump system according to claim 1, wherein the liquid supply channels are in the form of axially extending grooves on the surface of the axial extensions.

5. The pump system according to claim 1, wherein the axial extensions extend from opposite sides of a body of the rotor.

6. The pump system according to claim 1, wherein the rotor comprises one or more permanent magnets mounted close to a radial periphery of a body of the rotor.

7. The pump system according to claim 1, further comprising magnetic induction coils mounted in a stator part and acting on one or more permanent magnets mounted in the rotor to function as a step motor.

8. The pump system according to claim 1, further comprising a position sensor mounted in a stator part for detecting an axial position of the rotor.

9. The pump system according to claim 1, further comprising a reservoir containing a supply of liquid, the pump module being assembled to the reservoir and having an inlet in liquid communication with the reservoir.

10. The pump system according to claim 9, wherein the pump module is mounted on the reservoir and forms therewith a disposable liquid supply unit.

11. The pump system according to claim 1, further comprising an electronic control and communications module connected to magnetic induction coils for driving the rotor.

12. The pump system according to claim 11, wherein the electronic control and communications module comprises a RF transceiver for wireless communication with a user's display and control unit.

13. The pump system according to claim 1, wherein the rotor is primarily made of injected plastic material.

14. The pump system according to claim 13, wherein magnets are embedded by overmolding in a body portion of the rotor.

15. The pump system according to claim 1, wherein the stator housing is primarily made of injected plastic material.

16. The pump system according to claim 1, wherein the pump module comprises a RFID transponder storing information on calibration of the pump module related to the number of rotor revolutions as a function of the volume of liquid pumped.

17. The pump system according to claim 11, wherein the electronic control and communication module comprises a RFID reader for wireless communication with a RFID transponder mounted to a disposable liquid supply unit comprising the pump module.

* * * * *